US012643922B2

(12) United States Patent
Gerk

(10) Patent No.: US 12,643,922 B2
(45) Date of Patent: Jun. 2, 2026

(54) URSOLIC ACID PREPARATIONS AND USES THEREOF

(71) Applicant: VIRGINIA COMMONWEALTH UNIVERSITY, Richmond, VA (US)

(72) Inventor: Phillip Gerk, Mechanicsville, VA (US)

(73) Assignee: Virginia Commonwealth University, Richmond, VA (US)

( * ) Notice: Subject to any disclaimer, the term of this patent is extended or adjusted under 35 U.S.C. 154(b) by 507 days.

(21) Appl. No.: 18/263,626

(22) PCT Filed: Feb. 4, 2022

(86) PCT No.: PCT/US2022/015181
§ 371 (c)(1),
(2) Date: Jul. 31, 2023

(87) PCT Pub. No.: WO2022/170017
PCT Pub. Date: Aug. 11, 2022

(65) Prior Publication Data

US 2024/0101593 A1 Mar. 28, 2024

Related U.S. Application Data

(60) Provisional application No. 63/145,637, filed on Feb. 4, 2021.

(51) Int. Cl.

| | |
|---|---|
| ***A61K 31/56*** | (2006.01) |
| ***A61K 9/00*** | (2006.01) |
| ***A61K 9/107*** | (2006.01) |
| ***A61K 47/12*** | (2006.01) |
| ***A61K 47/28*** | (2006.01) |
| ***A61K 47/34*** | (2017.01) |
| ***C07J 63/00*** | (2006.01) |

(52) U.S. Cl.
CPC ........... *C07J 63/008* (2013.01); *A61K 9/0053* (2013.01); *A61K 9/1075* (2013.01); *A61K 31/56* (2013.01); *A61K 47/12* (2013.01); *A61K 47/28* (2013.01); *A61K 47/34* (2013.01)

(58) Field of Classification Search
CPC ..... C07J 63/008; A61K 9/1075; A61K 9/0053
See application file for complete search history.

(56) References Cited

U.S. PATENT DOCUMENTS

2016/0158147 A1 6/2016 Singer
2017/0281573 A1* 10/2017 Schwarz ............. A61K 9/2054

OTHER PUBLICATIONS

H.M. Sell and R.E. Kremers, "Metallic Salts of Ursolic Acid". Ind. Eng. Chem. Anal. Ed. 1935, 7, 2, 105â106. https://doi.org/10.1021/ac50094a009 (Year: 1935).*

Md. Akhlaquer Rahman, Arshad Hussain, Md. Sarfaraj Hussain, Mohd. Aamir Mirza & Zeenat Iqbal (2013) Role of excipients in successful development of selfemulsifying/microemulsifying drug delivery system (SEDDS/SMEDDS), Drug Development and Industrial Pharmacy, 39:1, 1-19. (Year: 2013).*

Hua WJ, Hua WX, Nan FY, Jiang WA, Yan C. The influence of herbal medicine ursolic acid on the uptake of rosuvastatin mediated by OATP1B1*1a and *5. Eur J Drug Metab Pharmacokinet. Sep. 2014;39(3):221-30. doi: 10.1007/s13318-014-0187-8. Epub Apr. 16, 2014. PMID: 24736980; PMCID: PMC4142139. (Year: 2014).*

Arruda MO et al. The Hydroalcoholic Extract Obtained from *Mentha piperita* L. Leaves Attenuates Oxidative Stress and Improves Survival in Lipopolysaccharide-Treated Macrophages. J Immunol Res. 2017;2017:2078794. doi: 10.1155/2017/2078794. Epub Sep. 20, 2017. PMID: 29085843; PMCID: PMC5632461. (Year: 2017).*

Graebin, C.S. (2018). The Pharmacological Activities of Glycyrrhizinic Acid (âGlycyrrhizinâ) and Glycyrrhetinic Acid. In: MÃ © rillon, JM., Ramawat, K. (eds) Sweeteners. Reference Series in Phytochemistry. Springer, Cham. https://doi.org/10.1007/978-3-319-27027-2_15 (Year: 2018).*

* cited by examiner

*Primary Examiner* — Rayna Rodriguez
*Assistant Examiner* — Oliver D Hees
(74) *Attorney, Agent, or Firm* — WCF IP

(57) ABSTRACT

Ursolic acid (UA) preparations and a self-nanoemulsifying drug delivery system (SNEDDS) composition containing at least one UA preparation selected from monopotassium ursolate (UAK), dipotassium ursolate (UAK2), monocholine ursolate (UAmC), dicholine ursolate (UAdC), pharmacological salts thereof, and mixtures thereof are provided. Methods for synthesizing UA preparations and delivering UA preparations to subjects in need thereof are also provided.

15 Claims, 7 Drawing Sheets

URSOLIC ACID PREPARATIONS AND USES THEREOF

FIELD OF THE INVENTION

The invention relates to divalent preparations of ursolic acid and pharmaceutical compositions thereof, methods of synthesizing ursolic acid salts or complexes, and methods of delivering ursolic acid preparations to a subject in need thereof.

BACKGROUND OF THE INVENTION

Ursolic acid is a naturally occurring plant substance and is a member of the pentacyclic triterpene class of compounds. Ursolic acid has been shown to display a number of useful pharmacological properties including anti-inflammatory activity, anti-viral activity, anti-oxidant activity, anti-tumor activity, liver protection, immune function enhancement, and lowering blood glucose.

At the molecular level, ursolic acid inhibits the STAT3 activation pathway, reduces matrix metalloproteinase-9 expression via the glucocorticoid receptor, inhibits protein tyrosine phosphatases, acts as an insulin mimetic, activates PPAR.alpha, inhibits NF-kB transcription factors, translocates hormone-sensitive lipase to stimulate lipolysis and inhibits the hepatic polyol pathway, among other effects.

Ursolic acid is poorly water-soluble with a solubility of less than 1 μg/mL in water. Oral ursolic acid has a bioavailability of less than 1%. Salt formation is one method used to increase solubility and dissolution rates of acidic and basic drugs. However, previously prepared monovalent salts of ursolic acid have provided limited improvement. Novel ursolic acid preparations having enhanced solubility are needed.

SUMMARY

The disclosure provides divalent ursolic acid (UA) salt preparations such as dipotassium ursolate (UAK2) and dicholine ursolate (UAdC) having increased solubility in hydrophilic solvents.

One aspect of the disclosure provides compositions, such as a self-nanoemulsifying drug delivery system (SNEDDS) composition, comprising at least one UA preparation, wherein the at least one UA preparation is selected from the group consisting of monopotassium ursolate (UAK), dipotassium ursolate (UAK2), monocholine ursolate (UAmC), ursolic acid dicholine complex (UAdC-O), ursolic acid dicholine hydroxide hydrated complex (UAdC-W), pharmacological salts thereof, and mixtures thereof, and at least two emulsifying agents. In some embodiments, the composition further comprises one or more compounds that inhibit sulfation of the at least one UA preparation. In some embodiments, the composition further comprises one or more compounds that inhibit glucuronidation of the at least one UA preparation.

Another aspect of the disclosure provides a method of synthesizing water-based dicholine ursolate (UAdC-W), comprising mixing ursolic acid and aqueous choline hydroxide in water to form a solution, heating the solution, cooling and incubating the solution at 20-25° C. until UAdC-W forms, and isolating UAdC-W. The disclosure further provides water-based dicholine ursolate (UAdC-W), wherein the UAdC-W is 10-25% water by mass.

Another aspect of the disclosure provides a method for increasing bioavailability of a ursolic acid (UA) preparation in a subject in need thereof, the method comprising orally administering a composition as described herein to the subject.

Additional features and advantages of the present invention will be set forth in the description of disclosure that follows, and in part will be apparent from the description of may be learned by practice of the disclosure. The disclosure will be realized and attained by the compositions and methods particularly pointed out in the written description and claims hereof.

DETAILED DESCRIPTION

Figure 1A:
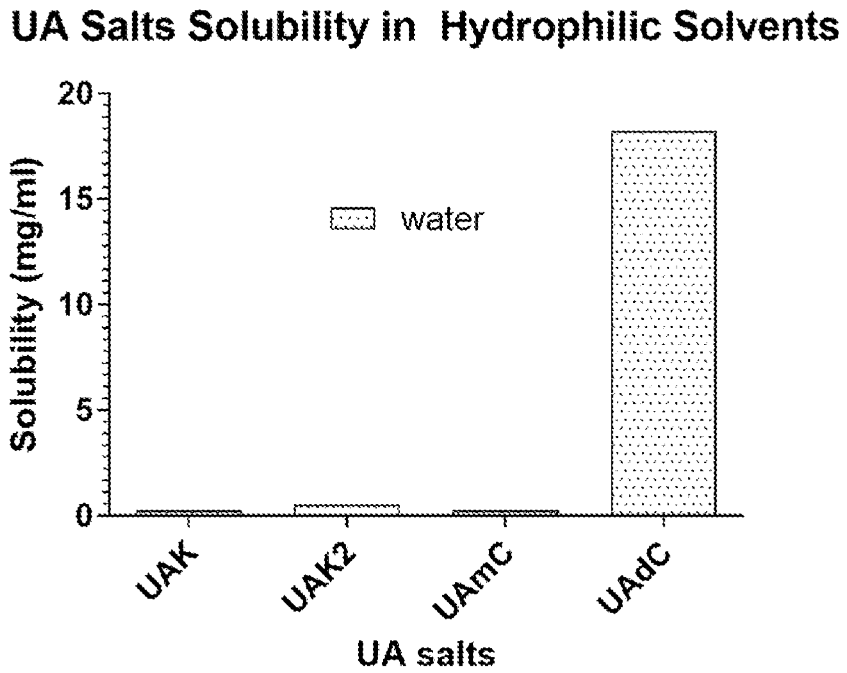
FIG. 1A-D. Ursolic acid salts solubility in hydrophilic solvents. Monopotassium (UAK), dipotassium (UAK2), monocholine (UAmC), and dicholine (UAdC-O) ursolic acid salt solubility in (A) water and (B) ethanol. (C) UA and UAdC-O solubility in water, PEG 400, glycerol, and ethanol. The salts were weighed, mixed with the solvent, and incubated to reach clear saturated solution (37° C. for water and ethanol; 55° C. for PEG 400 and glycerol). (D) The equilibrium (thermodynamic) solubility of ursolic acid originating from different preparations was measured using distilled water at 37° C. using the shake-flask method. After centrifugation and filtration, the supernatant was analyzed for ursolic acid by HPLC on a C-18 column followed by mass spectrometry ($[M-H]^-$=455.3) with comparison to known concentrations.

The preferred embodiments of the present disclosure are directed toward ursolic acid (UA) salts and compositions thereof and methods for increasing bioavailability of UA salt in a subject in need thereof by orally administering a composition as described herein to the subject.

Ursolic acid is a pentacyclic triterpene acid having the following formula:

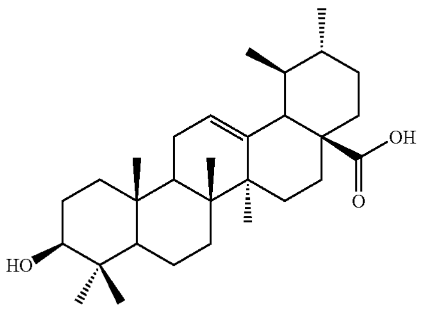

Ursolic acid is commercially available and is present in various plants from which it can be extracted, including apples, basil, bilberries, cranberries, elder flower, peppermint, rosemary, lavender, oregano, thyme, hawthorn, and prunes. It is used as a nutraceutical and pharmaceutical for various activities including anti-inflammatory, anti-cancer, and chemopreventive activities. It has also been shown to act as a COX-2 inhibitor and may be used to decrease body fat, decrease muscle loss, and increase muscle gain.

In some embodiments, the ursolic acid preparation is dipotassium ursolate (UAK2) having the following structure:

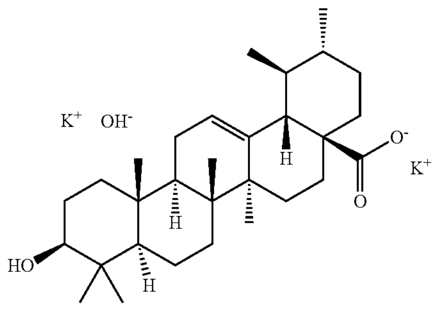

In some embodiments, the ursolic acid preparation is ursolic acid dicholine complex (UAdC-O) having the following structure:

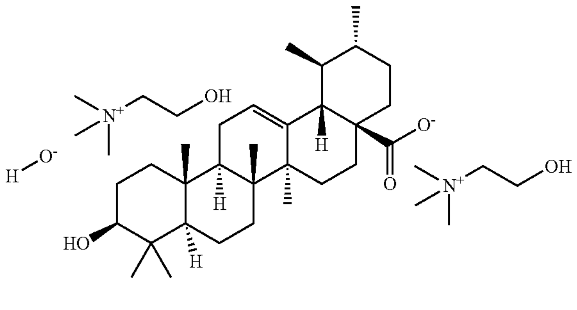

In some embodiments, the ursolic acid preparation is ursolic acid dicholine hydroxide hydrated complex (UAdC-W) having the following structure, where the number of hydrating water molecules is between 2 to 10:

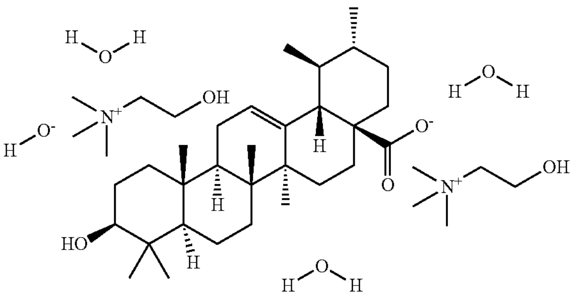

Embodiments of the disclosure provide pharmaceutical compositions comprising a UA salt complex or preparation as described herein. Such compositions may take various forms such as liquid-filled capsules, syrups, and a self-emulsifying formulation, such as a self-emulsifying drug delivery system (SEDDS), self-microemulsifying drug delivery system (SMEDDS), and self-nanoemulsifying drug delivery systems (SNEDDS). SEDDS, SMEDDS, and SNEDDS can be differentiated according to their size of globules upon aqueous dispersion. A lipid formulation classification system (LFCS) based on the composition was developed which categorized the LBF into four different types. The LFCS explains the formation of different types of self-emulsifying formulations in a very simple way based on their types and compositions. Briefly, Type I formulations represent 100% pure oil (surfactant free) as component. Types II and IIIA systems contain water insoluble surfactants (HLB<10) with different % oil in the formulation (Type II contain 60-80% oil and Type IIIA contain 40-60% oil). Type IIIB formulations contain water soluble surfactant and oil (20-50% oil), whereas Type IV formulations contain only water soluble surfactant/cosolvent without oil. Nanoemulsion fabrication methods are known in the art and comprise both high-energy and low-energy emulsification methods.

As used herein, the term "self-nanoemulsifying drug delivery system" or "SNEDDS" means anhydrous homogenous liquid mixtures comprising drug and at least two emulsifying agents or solubilizers which spontaneously form a nanoemulsion of approximately 20-200 nm (or less than 20 nm) in size upon dilution with water under gentle agitation. Nanoformulations with a particle size of less than 200 nm enhance permeability across the intestine. In some embodiments, the SNEDDS formulations may be filled in soft or hard gelatin capsules. Alternatively, hydroxypropyl methylcellulose (HPMC) capsules (moisture content 3-8%) may be useful for moisture-sensitive and hygroscopic products and whenever capsules of vegetable source need to be used. In order to provide sufficient drug solubility, hydrophilic organic solvents such as glycerol, dimethyl sulfoxide (DMSO), ethanol, isopropanol, propylene glycol, or benzyl alcohol (BA) may be utilized. In some embodiments, the solvent comprises polyethylene glycol (PEG), such as PEG 200, PEG 300, PEG 400, or PEG 600.

The compositions described herein may contain various types of UA salts, complexes, or preparations, such as monopotassium ursolate (UAK), dipotassium ursolate (UAK2), monocholine ursolate (UAmC), and dicholine ursolate (UAdC) which may be ursolic acid dicholine complex (UAdC-O) or ursolic acid dicholine hydroxide hydrated complex (UAdC-W).

Emulsifying agents or surfactants that may be included in compositions as described herein include, but are not limited to, polysorbates (Tweens®)), sorbitan esters of fatty acids (Spans®), Poloxamers®, lecithins, Gelucires®, Labrafils®, Labrasols®, Maisines®, tocopherols (e.g. vitamin E tocopherol polyethylene glycol succinate (TPGS)), cetearyl glucoside or poloxamers or other stabilizers such as ubiquinol, sodium dithionite, ascorbic acid, palmitoyl-ascorbic acid, xanthan gum, and propylene glycol alginate. Any of the forms or isomers of tocopherols and their derivatives, eg. esters may be used according to the present disclosure. Thus, for example, α-tocopherol can be used as such or in the form of its esters such as α-tocopherol acetate, linoleate, nicotinate or hemi succinate-ester, many of which are available commercially. The tocopherol derivative includes chemical derivatives of vitamin E with ester and ether linkages of various chemical moieties to polyethylene glycol of various lengths. For example, the derivative may include vitamin E tocopherol polyethylene glycol succinate (TPGS) derivatives with PEG molecular weights between about 500 and 6000 Da. In some embodiments, the vitamin E polymeric derivative is D-α-Tocopherol polyethylene glycol 1000 succinate (TPGS). In an embodiment, each emulsifying agent is present in the composition from about 5 wt % to about 60 wt %/volume, e.g. about 15-40 wt %. It should be understood that throughout the specification the term weight percent (wt %) refers to mass per unit volume, unless otherwise specified.

Compositions of the embodiments of the disclosure may also be adsorbed onto solid particles for the sake of transforming liquid, gel, or semi-solid formulations into flowable pharmaceutical powders to be encapsulated or tableted into solid oral dosage forms. Such solid adsorbents may include fumed silica or colloidal silica, povidone polymers, crospovidone polymers, alginates, microcrystalline cellulose, carboxymethylcellulose, and sugar spheres. Examples include Nu-SORB®, ProSolv®, VivaPharm®, VivaPur®, Zeopharm® 600, Aeroperl® 300, Syloids® (244FP, 63FP, XDP3150, XDP3050), and Aerosils® (200, R972)

Embodiments of the disclosure also include formulations and methods that enhance the pre-systemic survival of ursolic acid. Sulfation is one route of pre-systemic metabolism of ursolic acid in the intestine and liver. Embodiments include the reduction of pre-systemic metabolism using DME inhibitors. Further exemplary sulfation include inhibitors include, but are not limited to, triterpenoic acids such as glycyrrhetinic acid (licorice root extract) and oleanolic acid; obeticholic acid, abietic acid, dehydroepiandrosterone (DHEA), hederagenin, tomatidine (green tomato extract), carvacrol (oregano oil), lithocholic acid, ubiquinol, steviol, L-menthol, geraniol, bisabolol, linalool, hyodeoxycholic acid, ursodeoxycholic acid, deoxycholic acid, cholic acid, taurocholic acid, tauroursodeoxycholic acid, taurodeoxycholic acid, ox bile extract, curcumin, vanillin, quercetin, resveratrol, α-mangostin, ginger extract, and pterostilbene. In some embodiments, a weight percentage ratio range between the UA complex and the sulfation inhibitor compound is in the range from 1:0.1 to 1:10.

Another route of pre-systemic metabolism is glucuronidation. Embodiments of the disclosure include the reduction of pre-systemic metabolism using glucuronidation inhibitors. Exemplary glucuronidation inhibitors include, but are not limited to, chrysin, 6-gingerol, hesperidin, hesperetin, peppermint oil, α-mangostin, ginger extract, pterostilbene, quercetin, resveratrol, silybin, magnolol, geraniol, naringin, naringenin, curcumin. In some embodiments, a weight percentage ratio range between the UA complex and the glucuronidation inhibitor compound is in the range from 1:0.1 to 1:10.

Additional fatty acids that may be included in a formulation as described herein include, but are not limited to, conjugated linoleic acid, docosahexaenoic acid, eicosapentaenoic acid, arachidonic acid, linolenic acid, oleic acid, and alpha lipoic acid.

Additional molecules which may be incorporated in a formulation as described herein include bile acids, antihyperlipidemic drugs, antiseizure drugs, and anti-inflammatory drugs.

In some embodiments, the preparations, salts, or complexes described herein may be incorporated into another pharmaceutically acceptable carrier in a form suitable for therapeutic delivery to a subject. Another carrier or suspension for injections includes sterile saline, bacteriostatic water, Cremophor EL (BASF, Parsippany, NJ), phosphate buffered saline (PBS), ethanol or polyol (for example, glycerol, propylene glycol and polyethylene glycol and the like). The term "pharmaceutically acceptable carrier" as used herein refers to any and all solvents, dispersion media, coatings, isotonic and absorption delaying agents, and the like, that are compatible with pharmaceutical administration. The compositions may also contain other active compounds providing supplemental, additional, or enhanced therapeutic functions.

In some embodiments, the UA preparations, salts, or complexes described herein are useful for the same indications as UA per se. In some embodiments, the disclosure provides a method for: increasing skeletal muscle mass; treating skeletal muscle atrophy; treating sarcopenia; treating cachexia; increasing strength; treating weakness; increasing exercise capacity; treating fatigue; promoting muscle growth; promoting normal muscle function; improving muscle function; promoting muscle health; promoting healthy aging in muscles; increasing energy expenditure; increasing the ratio of skeletal muscle to fat; reducing fat; treating obesity; treating diabetes; lowering blood glucose; treating pre-diabetes; treating metabolic syndrome; treating insulin resistance; reducing plasma cholesterol; treating hypercholesterolemia; reducing plasma triglycerides; treating hypertriglyceridemia; promoting healthy metabolism; promoting metabolic health; treating hypertension; treating atherosclerosis; treating myocardial ischemia; treating myocardial infarction; treating cardiomyopathy; treating cardiac arrhythmia; treating non-alcoholic fatty liver disease (NAFLD); treating liver fibrosis; treating liver injury; treating lung injury; treating gastric ulcers; treating nephropathy; promoting bone formation; promoting normal bone structure; promoting bone health; treating osteoporosis; treating cerebral ischemia; treating cerebral hemorrhage; treating stroke; treating traumatic brain injury; treating dementia; treating Alzheimer's disease; treating memory loss; treating cognitive dysfunction; promoting normal cognitive function; treating anxiety; treating depression; reducing inflammation; treating arthritis; treating skin ulcers; treating skin wounds; promoting wound healing; treating skin dryness; treating skin roughness; treating skin scarring; treating skin wrinkles; reducing unwanted effects of aging; treating cancer; reducing tumor growth; treating tumor metastasis; treating tumor angiogenesis; increasing tumor cell apoptosis; decreasing protein oxidation; decreasing lipid oxidation; decreasing DNA oxidation; decreasing RNA oxidation; decreasing oxidation of cellular molecules; decreasing DNA damage; treating bacterial infection; reducing bacterial growth; treating fungal infection; reducing fungal growth; treating viral infection; treating protozoal infection; treating nematode infection; or treating a disease state, condition, or disorder mediated by activating transcription factor 4

(ATF4), in a subject, the method comprising administering to the subject an effective amount of a UA salt/complex or a composition comprising the UA salt/complex.

Further embodiments provide a method for increasing bioavailability of a UA salt/complex in a subject in need thereof, the method comprising orally administering a composition as described herein to the subject.

In some embodiments, the UA preparations, salts, or complexes are administered in a dosage ranging from about 0.001 to about 500 mg/kg of subject body weight including any and all ranges and subranges therein (e.g., 0.001 to 100 mg/kg, 0.01 to 75 mg/kg, 0.05 to 20 mg/kg, 0.1 to 10 mg/kg, etc.).

In some embodiments, the ursolic acid salts/complexes are administered in an amount of 1 to 2,000 mg including any and all ranges and subranges therein (e.g., 20 to 1900 mg, 50 to 1800 mg, 75 to 1700 mg, 100 to 1600 mg, etc.). Thus, in some embodiments where the ursolic acid salt/complex is administered in a composition, the composition will contain such amount of the compound.

In some aspects, one or more UA salts/complexes are administered simultaneously, separately, or sequentially with one or more therapeutic agents such as a cardiovascular, anti-inflammatory, anti-diabetic, or anti-cancer agent. When used in such a combination, the one or more therapeutic agents and the one or more UA salts/complexes can be administered as separate agents at the same or different times or they can be formulated as a single composition comprising both compounds.

The preparation methods described herein may be used to synthesize salts/complexes of other poorly water-soluble drugs. As used herein, the term "poorly water-soluble" or "lipophilic" refers to having a solubility in water at 20° C. of less than 1%, e.g., 0.01% (w/v), i.e., a "sparingly soluble to very slightly soluble drug" as described in Remington, *The Science and Practice of Pharmacy,* $19^{th}$ Edition, A. R. Gennaro, Ed., Mack Publishing Company, Vol. 1, p. 195 (1995). Examples of therapeutic classes of therapeutic compounds include, but are not limited to, antihypertensives, antianxiety agents, anticlotting agents, anticonvulsants, blood glucose-lowering agents, decongestants, antihistamines, antitussives, antineoplastics, beta (β)-blockers, anti-inflammatories, antipsychotic agents, cognitive enhancers, anti-atherosclerotic agents, cholesterol reducing agents, anti-obesity agents, autoimmune disorder agents, anti-impotence agents, antibacterial and antifungal agents, hypnotic agents, antibiotics, anti-depressants, anti-Parkinsonism agents, anti-Alzheimer's disease agents, antiviral agents and combinations of the foregoing.

Additional acidic drugs that may be included in a formulation as described herein include, but are not limited to, ibuprofen, ketoprofen, naproxen, and valproic acid. Examples include the HMG-CoA reductase inhibitors such as fluvastatin, lovastatin, atorvastatin, pravastatin, pitavastatin and others in this class; fluoroquinolones such as ciprofloxacin, ofloxacin, levofloxacin; β-lactam antibiotics such as cephalexin; angiotensin converting enzyme inhibitors such as enalaprilat, diuretics such as ethacrynic acid; arachidonic acid derivatives and metabolites such as dinoprost, prostaglandins, thromboxanes, prostacyclins; cholesterol-lowering fibric acid derivatives such as fenofibric acid, and dehydropeptidase inhibitors such as cilastatin.

Additional natural compounds that may be included in an embodiment include salvianolic acids A and B, curcumin, quercetin, chrysin, epigallocatechin gallate, epicatechin gallate, silybin, silibinin, silydianin, silychristin, abietic acid, and other acidic natural compounds.

The compositions of the disclosure may be administered orally. Formulations suitable for oral administration include solid formulations, such as tablets, capsules containing particulates, liquids, or powders; lozenges (including liquid-filled), chews; multi- and nano-particulates; gels, solid solution, liposome, films (including muco-adhesive), ovules, sprays and liquid formulations. The pharmaceutical composition may, for example, be in a form suitable for oral administration as a tablet, capsule, pill, powder, sustained release formulations, solution, or suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier and a compound according to the invention as an active ingredient. In addition, it may include other medicinal or pharmaceutical agents, carriers, adjuvants, etc.

The relative amounts of the active ingredient, the pharmaceutically acceptable carrier, and any additional ingredients in a pharmaceutical composition will vary, depending upon the identity, size, and condition of the subject treated and further depending upon the route by which the composition is to be administered. By way of example, the composition may comprise between 0.1% and 100% (w/w) active ingredient.

An effective amount of a composition sufficient to achieve a therapeutic or prophylactic effect should be determined by standard procedures used by medical professionals, e.g. physicians. The compositions described herein may be administered on multiple occasions. The interval between single doses can be daily, weekly, monthly, or yearly. Alternatively, the composition can be administered as a sustained release formulation. As noted above, dosage and frequency will vary depending on a plurality of considerations including the intended uses (i.e. prevention or treatment), efficacy and the half-life of the composition in a subject.

By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular, from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 10 mg/kg of body weight per day.

The active agent may be combined with pharmaceutically acceptable excipients. “Pharmaceutically” or “pharmaceutically acceptable” refer to molecular entities and compositions that do not produce an adverse, allergic or other untoward reaction when administered to a mammal, especially a human, as appropriate. A pharmaceutically acceptable carrier or excipient refers to a non-toxic solid, semisolid or liquid filler, diluent, encapsulating material or formulation auxiliary of any type. The compounds described herein are generally delivered (administered) in a pharmaceutical composition and the present disclosure encompasses such formulations/compositions. The pharmaceutical compositions generally comprise at least one of the disclosed compounds, i.e. one or more than one (a plurality of) different compounds in a single formulation. The compositions also generally include a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the compounds are mixed with excipients which are pharmaceutically acceptable and compatible with the compounds, e.g. pharmaceutically acceptable salts. Suitable excipients include, for example, water, saline, dextrose, glycerol, ethanol, propylene glycol, polyethylene glycols, and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added.

Capsules or tablets may also be enterically coated for the purpose of delaying the release of the formulation contents until reaching the intestine. Such enteric coatings include acrylic and methacrylic esters such as Eudragit® coatings, cellulose ester based coatings such as cellulose acetate phthalate, cellulose acetate, ethylcellulose, carboxymethylcellulose, and microcrystalline cellulose; sodium alginate and alginic acid coatings; polyvinyl alcohol coatings; shellac and shellac derivative-based coatings. Examples of these include Eudragit®, Nutrateric®, C-A-P®, VivaCoat®, NS Enteric®, and others.

“Pharmaceutically acceptable salts” refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed.

Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, piperidine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like. The compounds of the present disclosure include any polymorphs, solvates, and hydrates of the salts described herein.

In a particular embodiment, the subject is an animal. The animal may be selected from the group consisting of humans, non-human primates, cattle, horses, pigs, sheep, goats, dogs, cats, birds, chickens or other poultry, ducks, geese, pheasants, turkeys, quails, guinea pigs, rabbits, hamsters, rats, and mice.

Embodiments of the disclosure also provide methods of preparing or synthesizing salts/complexes and compositions and described herein. Typically, the base and the acid are either dissolved separately and then mixed together or dissolved together. To isolate the salt, the solvent is typically evaporated, or it may be precipitated by using an anti-solvent (see US Patent Publication 2014/0024708 and CN 102234304 incorporated herein by reference). The synthesis methods described herein can be used to make novel salts of other monoacidic compounds.

As discussed in the Example, at least two different methods of preparing the dicholine salt of ursolic acid (UAdC) may be used: organic solvent based (UAdC-O) and water based (UAdC-W). The two different methods give products with different characteristics. UAdC-O is a mixed crystalline and amorphous form, while UAdC-W is amorphous. UAdC-O is unstable, turning a dark color and decreasing in water solubility with time. In contrast, UAdC-W is stable, and has about a 6-fold greater water solubility compared to UAdC-O. Additionally, UAdC-W is 10-25% water by mass, and appears to form a stable complex. UAdC-W may form a salt-water complex, comprising one molecule of ursolic acid, two molecules of choline, and 2-10 molecules of stably-complexed water.

In an exemplary embodiment, a method of synthesizing UAdC-W comprises mixing ursolic acid and aqueous choline hydroxide in water to form a solution, heating the solution, cooling and incubating the solution under ambient conditions, e.g. 18-25° C., until UAdC-W forms, and isolating UAdC-W. The solution may be heated to a temperature of about 40-70° C. for about 10-30 minutes until a yellowish solution is formed.

The ursolic acid salts/complexes can be isolated from the reaction mixture by methods well known to those skilled in the art, including according to the method set forth in U.S. Pat. No. 3,957,853, which is incorporated herein by reference.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1

Example procedures for the synthesis of the dicholine salt/complex of ursolic acid (UAdC) are provided below.

Organic Solvent-Based (UAdC-O) Synthesis

Ursolic acid (1.43 g, 3.12 mmol) was completely dissolved in methanol or ethanol (200 ml) with heating (60° C.). Choline hydroxide in methanol (freshly prepared from potassium hydroxide and choline chloride) was added to supply 2 molar equivalents. The mixture was stirred at room temperature overnight, then dried down in a rotary evaporator at 50° C. Amorphous material was isolated and stored in a glass vial. UAdC-O has a formula weight of 681.06.

Water-Based (UAdC-W) Synthesis

Ursolic acid (2.3 g, 5.05 mmol) was combined with 2.66 g of aqueous choline hydroxide (47% w/w) with 24 ml water. The mixture was heated to 60° C. for 20 minutes, until a yellowish solution was formed. The solution was poured into plastic petri dishes (to a depth of about 5 mm) and allowed to sit at ambient conditions for 7 days. White flakes were isolated and stored in a glass vial. UAdC-W has a formula weight of in the range of 717.1 (dihydrate) to 861.2 (decahydrate). When UAdC-W was exposed to ambient indoor conditions for 470 days, the water content (loss on drying) was 18% w/w, consistent with the heptahydrate (FW 807.2).

Example 2

Several salts/complexes of ursolic acid were synthesized. Unexpectedly higher solubilities of the divalent salts of ursolic acid were found. This was unexpected, because ursolic acid has only one ionizable group at moderate pH values, which is its carboxylic acid (pKa 4.7). The hydroxyl group has an estimated pKa>15 (cf. viminalol, CAS #635-95-9: pKa 15.18, estimated by SciFinder® Scholar), so this group was not expected to be ionizable. One skilled in the art would expect to form monovalent salts of this monovalent molecule, as taught in U.S. patent application Ser. No. 13/698,645 incorporated herein by reference.

Figure 1B:
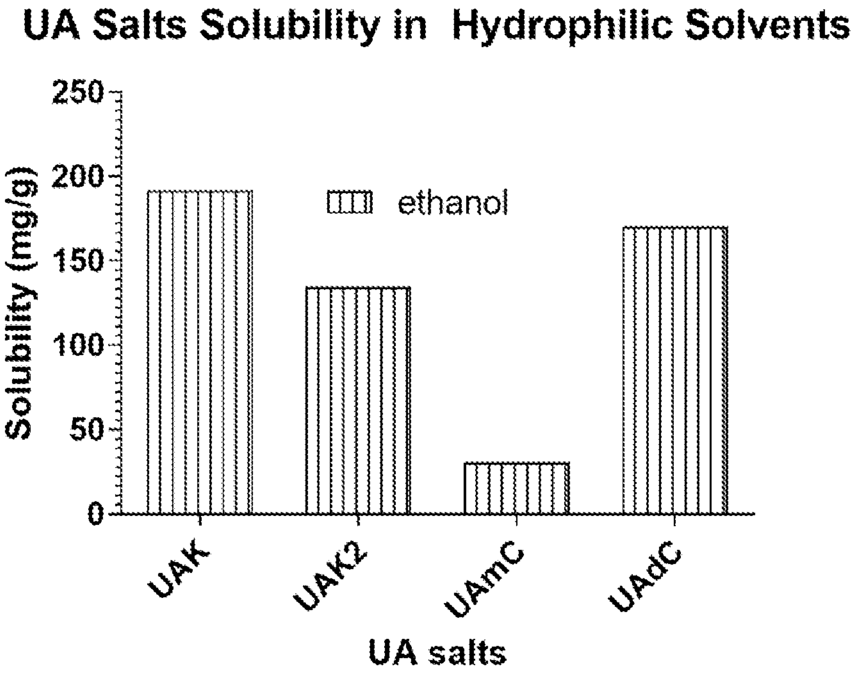
Figure 1C:
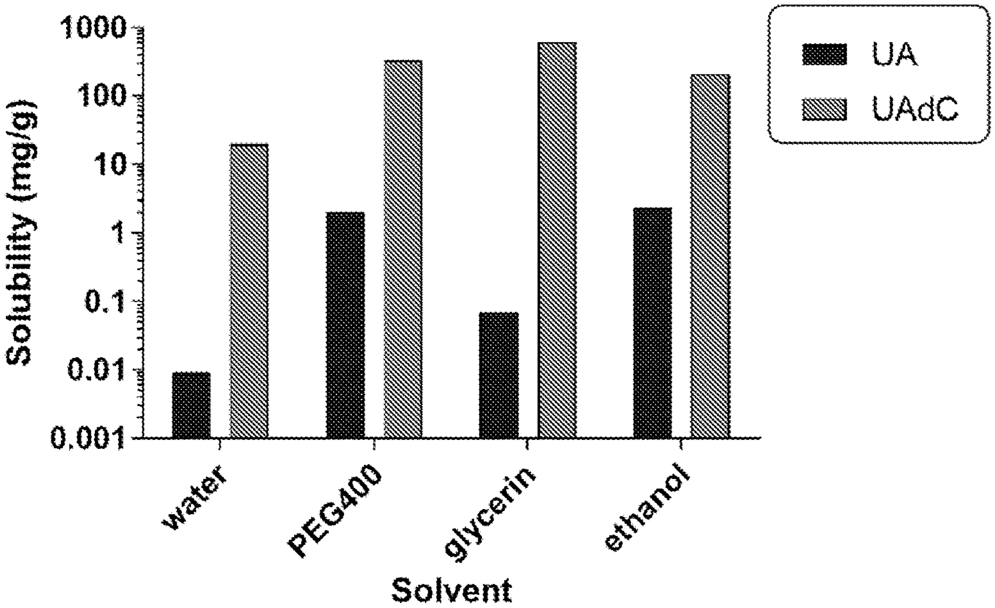
Figure 1D:
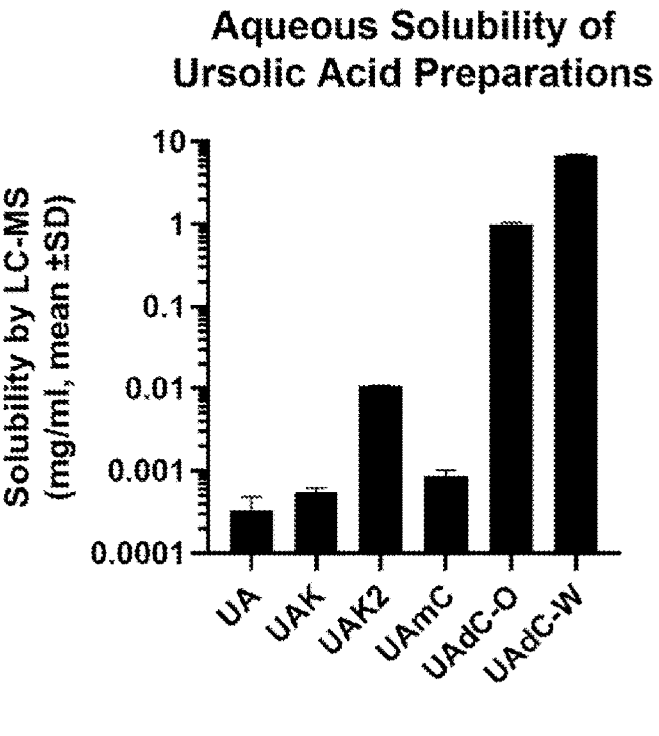

Ursolic acid (UA) itself has a predicted aqueous solubility of 0.07 μg/ml (GastroPlus® software). In the present study, it was found that the solubility of monopotassium ursolate (UAK) and dipotassium ursolate (UAK2) are <0.5 mg/g, and that monocholine ursolate (UAmC) was similar (0.54 mg/g) (FIG. 1A). However, dicholine ursolate (UAdC-O) water solubility was 18.2 mg/g, an unexpected 33.7-fold enhancement over UAmC. In a PEG400 solvent, UAK2 showed a modest 2.6-fold improvement in PEG400 solubility over UAK, but UAdC-O showed 27-fold solubility improvement over UAmC, despite the lower solubility of UAmC compared to UAK (data not shown). In glycerol, both UAK2 and UAdC-O showed 16-fold and 43-fold improvements over their respective monovalent salts (data not shown). In ethanol, UAK2 solubility is decreased compared to UAK, and UAmC solubility is less than UAK, but UAdC-O solubility far exceeds them all (FIG. 1B). UAdC-O showed enhanced solubility compared to ursolic acid in all solvents tested (FIG. 1C). FIG. 1D shows the aqueous solubility of several ursolic acid preparations including both UAdC-O and UAdC-W.

Figure 2:
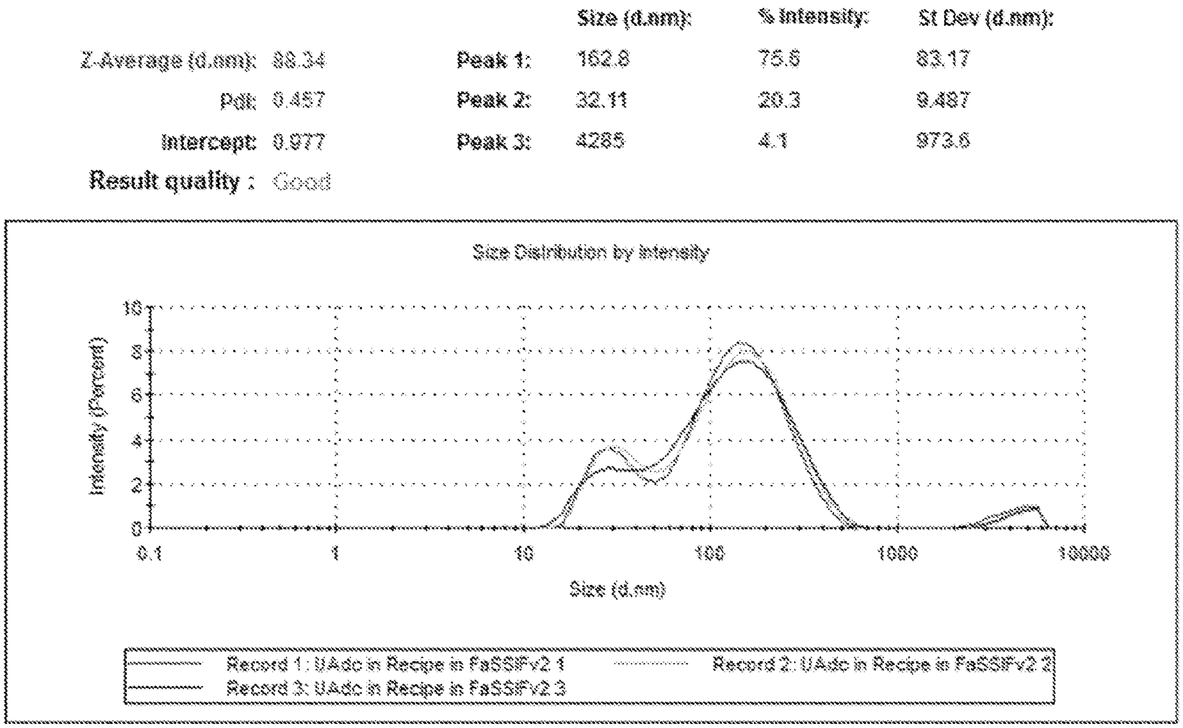
FIG. 2. Size distribution of UAdC formulation in Fasted State Simulated Intestinal Fluid (FaSSIF). The formulation contains 200 mg UAdC, 615 mg PEG 400, 123 mg vitamin E TPGS, 62 mg polysorbate 80, and HPMC "veggie" capsules.
Figure 3:
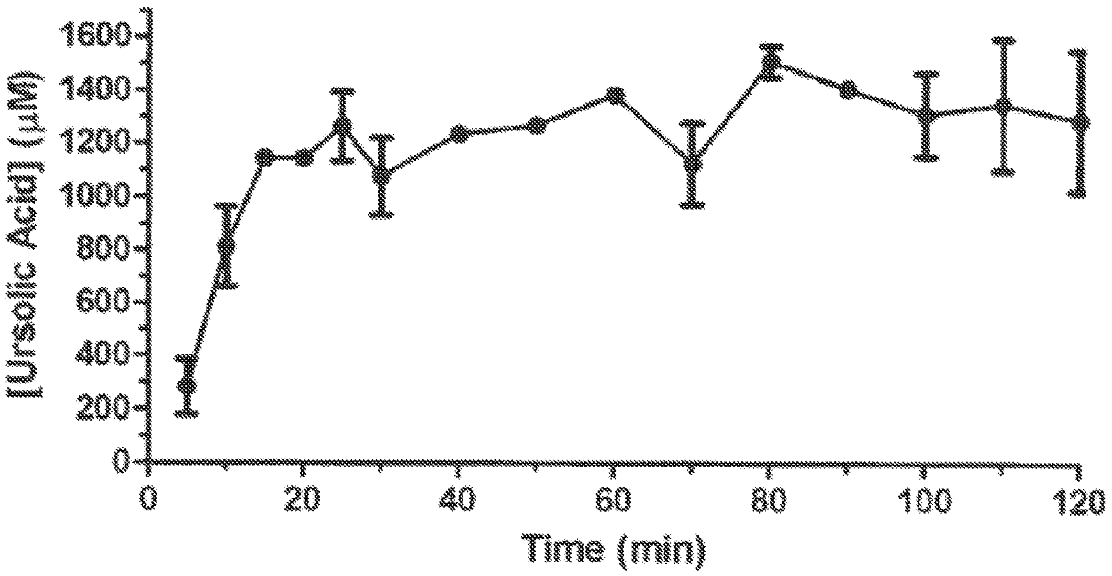
FIG. 3. Dissolution testing of UAdC formulation. The formulation is the same as that described in FIG. 2. 250 ml of FaSSIF (USP <1236>) was added and paddle stirred (50 rpm) at 37° C. The samples were filtered (0.2 μm PES), centrifuged (14,000 rcf; 15 minutes), mixed with methanol, and then analyzed by HPLC-MS (m/z 455).

FIGS. 2 and 3 show that when UAdC is combined with a self-nanoemulsifying drug delivery system (SNEDDS), a nanoparticle dispersion is formed, having biorelevant solubility in excess of 1 mM.

Figure 4:
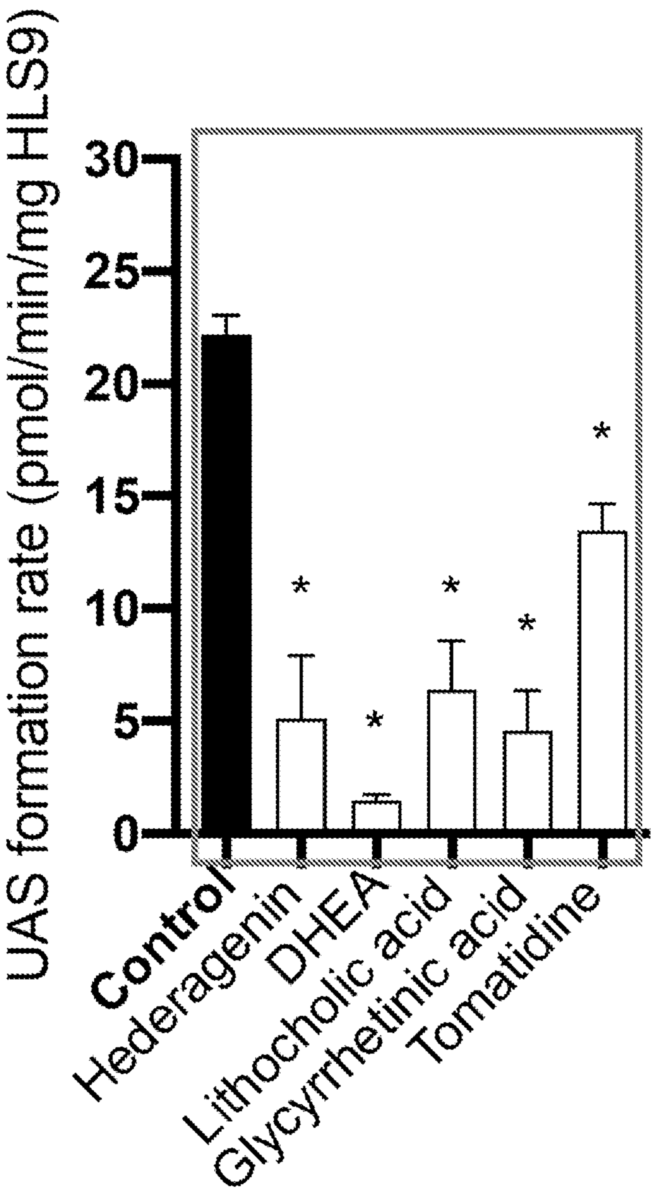
FIG. 4. Screening of sulfation inhibitors. Asterisk indicates P<0.01. UA concentration was 2 μM. Inhibitor concentrations were 8 μM. Data were pooled from two experiments in HLS9 (performed in two and three replicates, respectively), and therefore each data set represents five replicates.
Figure 5:
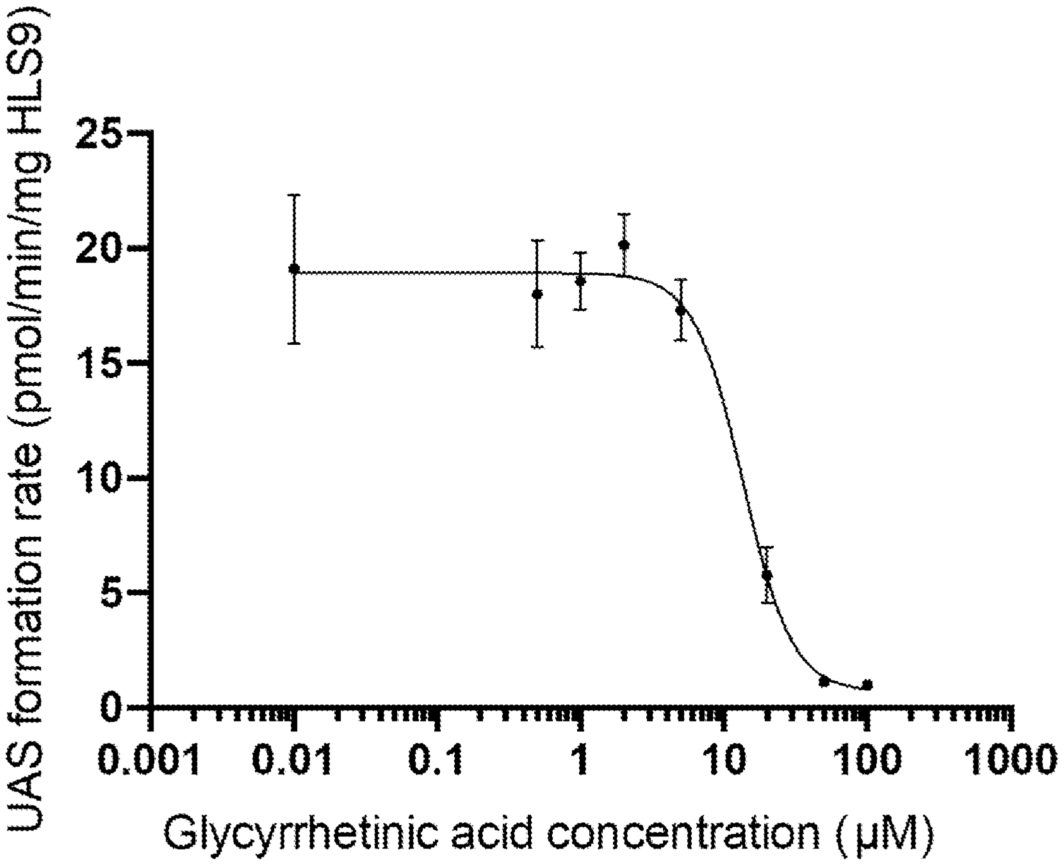
FIG. 5. $IC_{50}$ of glycyrrhetinic acid. UA concentration was 2 μM. Determination was done in triplicate. $IC_{50}$: 18.6 (95% CI: 11.0, 32.7).

FIG. 4 shows that several sulfation inhibitors are effective in reducing the sulfation of ursolic acid. Sulfation inhibitors may thus be used to reduce presystemic metabolism of ursolic acid. FIG. 5 shows the $IC_{50}$ of the sulfation inhibitor glycyrrhetinic acid in particular.

Example 3

Table 1 shows that several natural products or dietary supplements can effectively inhibit the presystemic sulfation of UA, thus enhancing the oral bioavailability of UA. The data show that bile acids and lipophilic compounds with steroid-like structures can inhibit sulfation of UA.

Table 1. $IC_{50}$ values for several inhibitors of UA sulfation. UA concentration was 2 μM. Determinations were done in triplicate, and formation of UA-sulfate was determined by HPLC-MS followed by nonlinear regression with the Hill equation.

| Inhibitor | $IC_{50}$ (μM) | Hill slope |
|---|---|---|
| Glycyrrhetinic acid | 14.0 ± 0.2 | 4.8 ± 3.5 |
| Tomatidine | 84.8 ± 5.1 | 0.5 ± 0.03 |
| Lithocholic acid | 18.1 ± 2.4 | 1.9 ± 0.7 |
| DHEA | 1.2 ± 0.1 | 1.4 ± 0.1 |
| 7-oxo-DHEA acetate | 20.2 ± 3.6 | 1.2 ± 0.06 |
| 7-oxo-DHEA | 38.1 ± 1.2 | 1.2 ± 0.4 |
| Steviol | 11.8 ± 1.8 | 1.4 ± 0.1 |

Figure 6:
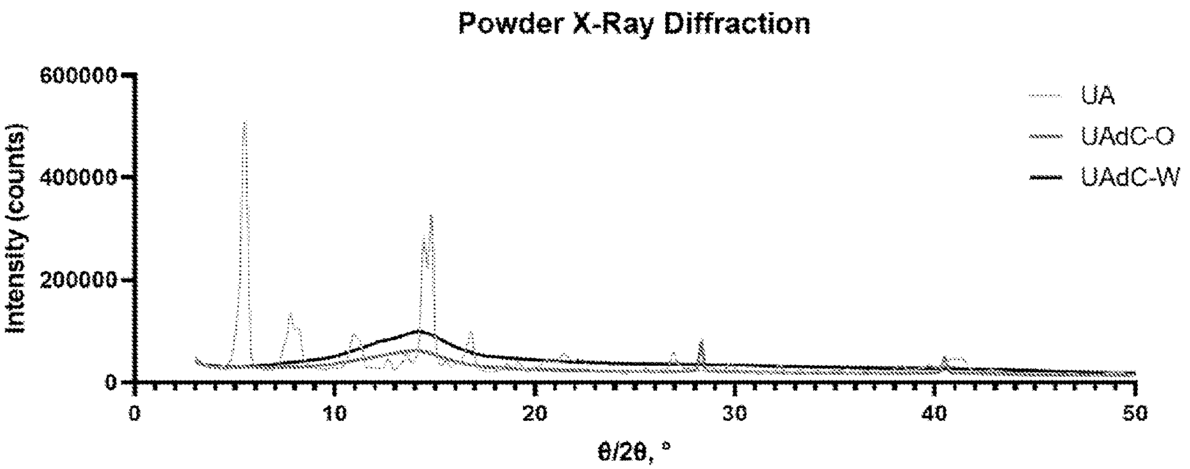
FIG. 6. Powder X-Ray Diffraction of UA, UAdC-O, and UAdC-W.

FIG. 6 shows Powder X-Ray Diffraction (PXRD) of the complexes we made. PXRD is commonly used to determine the extent to which a solid substance is crystalline or amorphous. Pure UA is extensively crystalline, as shown by the many sharp peaks observed on PXRD. UAdC-O is mainly amorphous, but does have some crystalline character, as evidenced by the peaks at 28.4° and 40.5°. In contrast, UAdC-W is entirely lacking sharp peaks, indicating that the material is amorphous. Notably, amorphous materials are well known by those skilled in the art to enhance solubility in the gastrointestinal tract and thereby enhance oral absorption and bioavailability.

Figure 7:
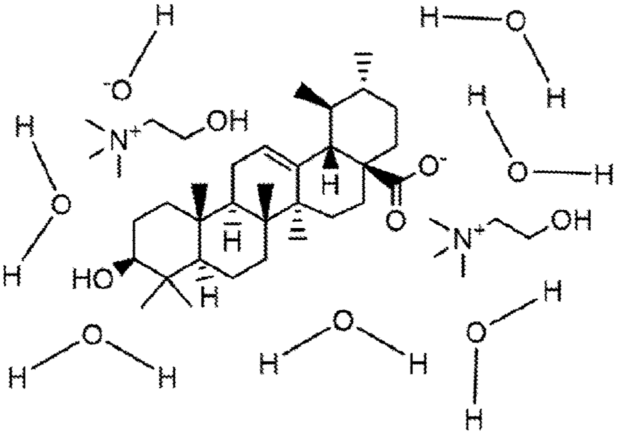
FIG. 7. Composition of UAdC-W determined by elemental analysis.

FIG. 7 provides data from elemental analysis of UAdC-W. Elemental analysis was used to determine the choline and water content of UAdC-W. The data are consistent with one molecule of ursolic acid (as the ursolate anion), two molecules of choline hydroxide (as two molecules of cholinium and one molecule of hydroxide), and a total of 6 molecules of water (including one released from neutralization of the acidic proton of ursolic acid by a hydroxide). The structure of the complex is shown in the figure. UAdC-W (dicholine hydroxide ursolate, hexahydrate): FW 789.15; $C_{40}H_{88}N_2O_{12}$ calculated C 60.88, H 11.24, N 3.55; found C 61.52, H 10.83, N 3.72.

Figure 8:
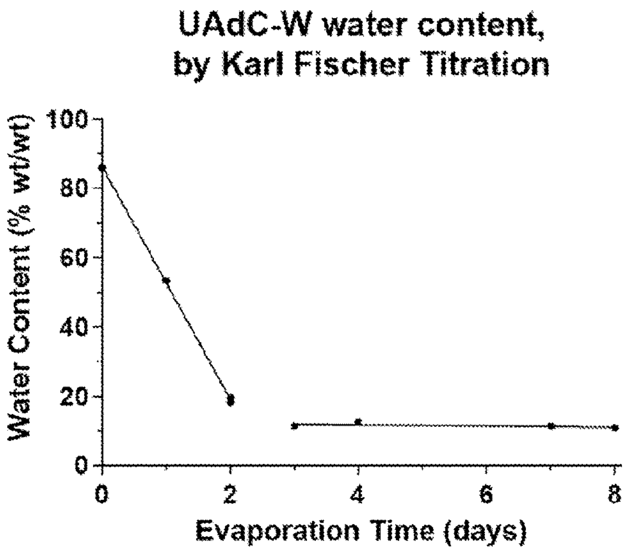
FIG. 8. Equilibration time for the formation of UAdC-W complex. Water content was determined by Karl Fischer volumetric titration.

In FIG. 8, the equilibration time for the formation of the UAdC-W complex was investigated. As shown above, within one week a stable complex was achieved. Using Karl Fischer titrations, our preparations typically comprise complexes including water in the range of 12-20% w/w.

Figure 9A:
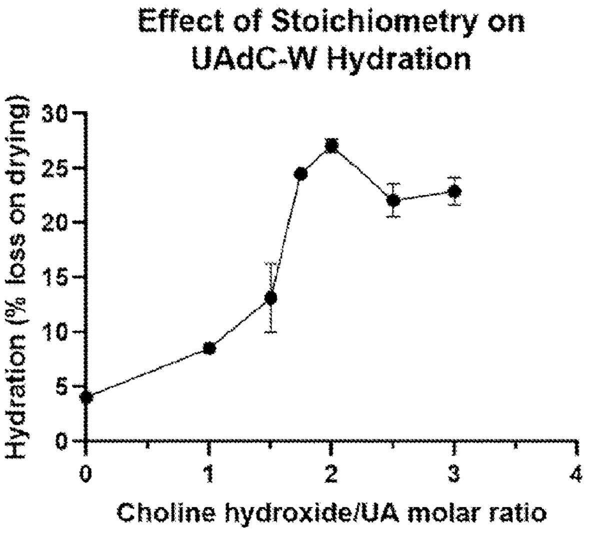
FIG. 9A-B. Varying ratios of choline hydroxide to ursolic acid were mixed to determine the stoichiometry of the complex regarding the retention of water (A) and the water solubility of the complex (B).
Figure 9B:
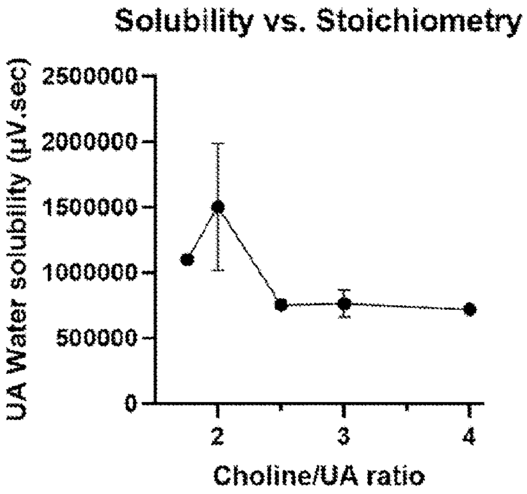

In FIG. 9 the stoichiometric relationship between choline hydroxide and ursolic acid was investigated with respect to the effects on the retention of water (A) and the water solubility of the complex (B). Varying ratios of choline hydroxide: ursolic acid were combined in water and allowed to dry for 5 days under ambient conditions, as described. In FIG. 9A, samples were weighed before and after drying at 130° C. for 100 minutes to determine water loss (w/w). The data show that there was a sharp increase in hydration of the complex at a molar ratio of 2, but hydration dropped off above 2. Thus, the stoichiometry of the complex ideally comprises a choline hydroxide: ursolic acid ratio of 2 for optimal hydration. In FIG. 9B, Samples were mixed with water and shaken for several hours, followed by separation of the soluble liquid from the insoluble matter, then analyzed by HPLC-MS. As shown above, solubility of UA was highest at a molar ratio of 2, but decreased at ratios above. Thus the stoichiometry of the complex ideally comprises a choline hydroxide: ursolic acid ratio of 2 for optimal water solubility.

What is claimed is:

1. An ursolic acid salt, wherein the salt is dipotassium ursolate (UAK2) of formula:

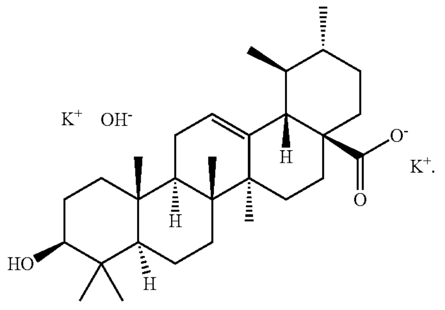

2. An ursolic acid complex, wherein the complex is ursolic acid dicholine complex (UAdC-O) of formula:

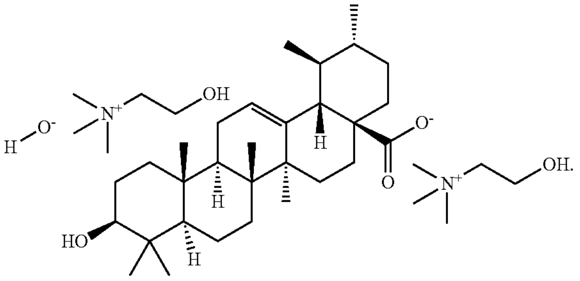

3. An ursolic acid complex, wherein the complex is ursolic acid dicholine hydroxide hydrated complex (UAdC-W) of formula below, where the number of complexed water molecules ranges between 2 and 10:

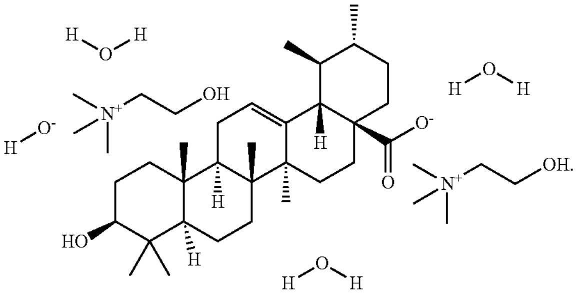

4. A self-nanoemulsifying drug delivery system (SNEDDS) composition comprising:

at least one ursolic acid (UA) preparation, wherein the at least one UA preparation is selected from the group consisting of dipotassium ursolate (UAK2), ursolic acid dicholine complex (UAdC-O), ursolic acid dicholine hydroxide hydrated complex (UAdC-W), pharmacological salts thereof, complexes thereof, and mixtures thereof; and at least two emulsifying agents.

5. The composition of claim 4, wherein the at least one UA preparation is UAK2.

6. The composition of claim 4, wherein the at least one UA preparation is UAdC-O.

7. The composition of claim 4, wherein the at least one UA preparation is UAdC-W.

8. The composition of claim 4, wherein the at least two emulsifying agents are selected from the group consisting of polyethylene glycol 400, D-α-tocopheryl polyethylene glycol succinate (vitamin E TPGS), and polysorbate 80.

9. The composition of claim 4, further comprising one or more compounds that inhibit sulfation of the at least one UA preparation.

10. The composition of claim 9, wherein the one or more compounds that inhibit sulfation are selected from the group consisting of glycyrrhetinic acid, hederagenin, dehydroepiandrosterone (DHEA), lithocholic acid, tomatidine, 7-OXO-DHEA, 7-oxo-DHEA acetate, steviol, deoxycholic acid, and ox bile extract.

11. The composition of claim 4, further comprising one or more compounds that inhibit glucuronidation of the at least one UA preparation.

12. The composition of claim 11, wherein the one or more compounds that inhibit glucuronidation are selected from the group consisting of chrysin, 6-gingerol, hesperidin, hesperetin, peppermint oil, α-mangostin, ginger extract, pterostilbene, quercetin, resveratrol, silybin, magnolol, geraniol, naringin, naringenin, and curcumin.

13. A method of synthesizing ursolic acid dicholine hydroxide hydrated complex (UAdC-W), comprising:

mixing ursolic acid and aqueous choline hydroxide in water to form a solution;

heating the solution;

cooling and incubating the solution at 20-25° C. until UAdC-W forms; and isolating UAdC-W.

14. The method of claim 13, wherein the UAdC-W is 10-25% water by mass.

15. A method for increasing bioavailability of a ursolic acid (UA) preparation in a subject in need thereof, the method comprising orally administering the composition of claim 4 to the subject.

* * * * *